United States Patent [19]

Izumi

[11] Patent Number: 5,225,547
[45] Date of Patent: Jul. 6, 1993

[54] REACTION ACCELERATOR FOR REARRANGEMENT OF OXIME TO AMIDE AND PROCESS FOR PRODUCING AMIDES BY REARRANGEMENT OF OXIMES

[75] Inventor: Yusuke Izumi, 907, Hara-4-chome, Tenpaku-ku, Nagoya-shi, Japan

[73] Assignees: Sumitomo Chemical Company Limited; Yusuke Izumi, both of Osaka, Japan

[21] Appl. No.: 715,767

[22] Filed: Jun. 14, 1991

[30] Foreign Application Priority Data

Jun. 15, 1990 [JP] Japan .................... 2-158498

[51] Int. Cl.$^5$ .............. C07D 201/04; C07C 223/00; C07C 239/00
[52] U.S. Cl. .................... 540/535; 564/215; 564/216; 564/218
[58] Field of Search ............... 540/535; 564/215, 216, 564/218

[56] References Cited

U.S. PATENT DOCUMENTS 3,944,542  3/1976  de Rooij et al. .................... 540/553

FOREIGN PATENT DOCUMENTS 62-149665  7/1987  Japan .
572033  1/1976  Switzerland .................... 340/553

OTHER PUBLICATIONS

Office Action (Taiwan).
March "Advanced Organic Chemistry" (1968) pp. 820—812 (McGraw-Hill).
Chemistry Letters, vol. 12, 1990, pp. 2171–2174; Y. Izumi: "Catalytic Beckmann Rearrangement of Oximes in Homogeneous Liquid Phase".
Patent Abstracts of Japan, vol. 1, No. 13, Mar. 22, 1977, p. 713C76; & JP-A-51127090 (Ube Kosan K.K.) May 11, 1976.
Journal of Organic Chemistry, vol. 36, No. 15, 1971, pp. 2159–2161; K. Kelly et al.: "The Use of Lewis Base--Sulfur Trioxide Complexes as Reagents for the Beckmann Rearrangement of Ketoximes".
Egypt. J. Chem. 16, No. 6, pp. 551–553 (1973).

*Primary Examiner*—Robert T. Bond
*Attorney, Agent, or Firm*—Stevens, Davis, Miller & Mosher

[57] ABSTRACT

A reaction accelerator for rearrangement of an oxime to an amide consisting of an alkylating agent and an N,N-disubstituted formamide or N,N-disubstituted carboxylic acid amide represented by formula (1):

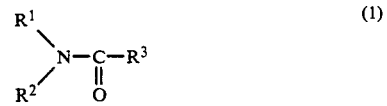

wherein $R^1$ and $R^2$, which may be the same or different, represent alkyl groups having 1 to 6 carbon atoms or substituted or unsubstituted phenyl groups having 6 to 9 carbon atoms, and $R^3$ represents a hydrogen atom or an alkyl group having 1 to 6 carbon atoms. An amide can effectively be produced by rearranging a corresponding oxime in the presence of said reaction accelerator.

15 Claims, No Drawings

REACTION ACCELERATOR FOR REARRANGEMENT OF OXIME TO AMIDE AND PROCESS FOR PRODUCING AMIDES BY REARRANGEMENT OF OXIMES

This invention relates to a reaction accelerator for rearrangement of an oxime to an amide and a process for producing an amide by rearrangement of an oxime using the reaction accelerator.

Rearrangement of an oxime to an amide is known as Beckmann rearrangement. For example, in the production of ε-caprolactam by rearrangement of cyclohexanone oxime, fuming sulfuric acid has been used as a reaction accelerator in industry. However, in processes in which sulfuric acid is used, there is an essential problem that a large amount of ammonium sulfate is produced as a by-product, and there are many other problems such as corrosion of apparatus and the like. Thus, a development of a reaction accelerator or catalyst for efficient rearrangement has been desired.

For example, a solid oxide catalyst in which boron oxide is supported on silica, alumina or titania and a zeolite catalyst have been proposed. However, when these solid catalysts are used in rearrangement reactions, it is necessary to adopt gas phase reaction at high temperatures, so that the reaction is accompanied by a reduction of ε-caprolactam yield, a degradation of catalyst and an increase of energy cost. Therefore, the use of the solid catalysts has a problem in commercial production.

The inventors of this invention have made extensive research on reaction accelerators for rearrangement of oximes to corresponding amides to solve the above problems, and have consequently found that a system consisting of a combination of an alkylating agent and a specific N,N-disubstituted formamide or carboxylic acid amide can greatly accelerate the above rearrangement as a reaction accelerator or catalyst.

An object of this invention is to provide a process for producing an amide by rearrangement of a corresponding oxime.

Another object of this invention is to provide a process for producing an amide by rearrangement of a corresponding oxime at a moderate temperature under liquid phase conditions.

A further object of this invention is to provide a process for producing an amide by rearrangement of a corresponding oxime using a specific reaction accelerator or catalyst.

A still further object of this invention is to provide a reaction accelerator effective to the rearrangement of an oxime to a corresponding amide.

Other objects and advantages of this invention will become apparent from the following description.

According to this invention, there is provided a reaction accelerator for rearrangement of an oxime to a corresponding amide, which consists of an alkylating agent and an N,N-disubstituted formamide or carboxylic acid amide represented by formula (1):

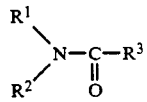
(1)

wherein $R^1$ and $R^2$, which may be the same or different, represent alkyl groups having 1-6 carbon atoms, substituted or unsubstituted phenyl groups having 6-9 carbon atoms, and $R^3$ represents a hydrogen atom or an alkyl group having 1-6 carbon atoms.

This invention further provides a process for producing an amide which comprising rearranging an oxime in the presence of the above-mentioned reaction accelerator.

The alkylating agent used in this invention are compounds having an alkylating activity such as alkanesulfonic acid esters, aromatic sulfonic acid esters, trialkyloxonium salts and sulfuric acid esters.

Specifically, the alkylating agent includes methyl methanesulfonate, ethyl methanesulfonate, methyl trifluoromethanesulfonate, ethyl trifluoromethanesulfonate, methyl benzenesulfonate, ethyl benzenesulfonate, methyl toluenesulfonate, ethyl toluenesulfonate, trimethyloxonium tetrafluoroborate, trimethyloxonium hexafluoroantimonate, dimethyl sulfate, diethyl sulfate, and 1,3-propanesultone.

A combination of compounds capable of forming the alkylating agent by reaction of the compounds may be used in place of direct use of the above-mentioned alkylating agent.

Specifically, the combination includes a combination of a strong acid, an ester thereof or a strong acid chloride with an epoxy compound, and a combination of triphenylmethyl perchlorate with an epoxy compound.

The strong acid includes boron trifluoride etherate, sulfuric acid, sulfuric anhydride, fuming sulfuric acid, perchloric acid, fluorosulfonic acid, heteropolyacids, alkanesulfonic acids, trifluoromethanesulfonic acid, benzenesulfonic acid, toluenesulfonic acid, sulfonic acid type ion exchange resins, and phosphorus pentoxide.

The epoxy compound may be any known epoxy compound. Specifically, the epoxy compound includes ethylene oxide, propylene oxide, 1,2-epoxybutane, isobutylene oxide, 1,2-epoxyoctane, 2,3-epoxyoctane, 1,2-epoxyhexadecane, cyclohexene oxide, 2,3-epoxynorbornane, styrene oxide, epichlorohydrin, epibromohydrin, 1,1,1-trichloro-2,3-epoxypropane, N-(2,3-epoxypropyl)phthalimide, glycidyl methacrylate, and glycidyl methyl ether. It also includes high molecular weight compounds having an epoxy group such as a polymer of glycidyl methacrylate and the like.

The N,N-disubstituted formamide and N,N-disubstituted carboxylic acid amide used in this invention are represented by formula (1):

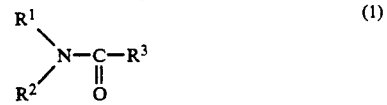
(1)

wherein $R^1$ and $R^2$, which may be the same or different, represent alkyl groups having 1-6 carbon atoms, substituted or unsubstituted phenyl groups having 6-9 carbon atoms, and $R^3$ represents a hydrogen atom or an alkyl group having 1-6 carbon atoms. The alkyl group having 1-6 carbon atoms includes methyl, ethyl, propyl, butyl, pentyl and hexyl, and the substituted or unsubstituted phenyl groups having 6-9 carbon atoms include phenyl, tolyl, xylyl, cumyl and mesityl.

Preferable examples of the N,N-disubstituted formamide are N,N-dimethylformamide, N,N-diethylformamide, N,N-dipropylformamide, N,N-diisopropylformamide, N,N-dibutylformamide, and N-phenyl-N-methylformamide.

Preferable examples of the N,N-disubstituted carboxylic acid amide are N,N-dimethylacetamide, N,N-dimethylpropionamide, N,N-dimethylbutyramide, N,N-dimethylvaleramide, N,N-dimethylcapronamide, N,N-diethylacetamide, N,N-diisopropylacetamide, and N,N-dimethylisobutyramide.

The amount of the above reaction accelerator used is not critical; however, it is preferable that the amount of the alkylating agent be in a range of about 1 to 250 mole % of the oxime, and the amount of the N,N-disubstituted formamide or carboxylic acid amide be at least about 1 mole per mole of the alkylating agent.

The present reaction accelerator of an oxime to an amide can be applied to rearrangement of any known oxime compound.

Specific examples of the oxime include acetaldehyde oxime, acetone oxime, 2-butanone oxime, benzaldehyde oxime, acetophenone oxime, benzophenone oxime, cyclopentanone oxime, cyclohexanone oxime, and cyclododecanone oxime.

In the production of an amide by rearrangement of an oxime in the presence of the reaction accelerator of this invention, the rearrangement reaction can be effected in the presence or absence of a solvent. In general, the N,N-disubstituted formamide or carboxylic acid amide, which is one of the constituents of the reaction accelerator, is used as a solvent; however, if necessary, there may be used a hydrocarbon solvent such as benzene, toluene, hexanone, heptanone or the like; a halogenated hydrocarbon solvent such as 1,2-dichloroethane or the like; a non-protonic organic solvent such as dimethylsulfoxide or the like; etc.

The amount of the solvent is not critical; however, the solvent is generally used in such an amount that the oxime concentration in the reaction system is about 1 to 30% by weight, preferably about 5 to 25% by weight.

In this invention, it is necessary that the starting materials and the like do not contain water because water affects adversely rearrangement of oxime.

The method of rearranging an oxime using the reaction accelerator of this invention is generally preferably effected by feeding to a reactor a solution of the above-mentioned oxime and reaction accelerator in a solvent and subjecting them to reaction at a predetermined temperature.

When the N,N-disubstituted formamide, which is one of the constituents of the reaction accelerator, is used, rearrangement reaction occurs by mixing the oxime, N,N-disubstituted formamide, and alkylating agent, and then heating the resulting mixture.

However, when the N,N-disubstituted carboxylic acid amide is used, it is necessary that the reaction accelerator be previously prepared by mixing the N,N-disubstituted carboxylic acid amide with an alkylating agent and, if necessary, heating the resulting mixture, and then added to the oxime.

When a combination of compounds capable of forming an alkylating agent, which is one of the constituents of the reaction accelerator, is used as the alkylating agent, it is preferable to add the compounds to the N,N-disubstituted formamide or carboxylic acid amide and, if necessary, heat the resulting mixture to previously prepare the reaction accelerator, after which the reaction accelerator is added to a solvent in which the oxime is dissolved and the resulting mixture is subjected to rearrangement reaction.

When the reaction accelerator is a solid which is not dissolved in a solvent, the reaction is effected in the state that the reaction accelerator is suspended in the solvent or effected in a flow reactor in which the reaction accelerator is present in the form of a fixed layer.

The reaction temperature is generally about 20° to 150° C., preferably about 30° to 100° C.

The use of the reaction accelerator of this invention enables an amide to be obtained from a corresponding oxime in a high yield. In addition, according to the present process, the reaction conditions are moderate and the reaction is effected in the liquid phase, so that the reaction apparatus is not corroded and the energy cost can be reduced.

Moreover, unlike a conventional rearrangement method in which a large amount of sulfuric acid is used, the reaction accelerator of this invention can efficiently accelerate rearrangement reactions even when used in a catalytic amount, and therefore, can greatly inhibit the formation of by-products. Therefore, this invention is very useful in producing an amide on a commercial scale.

This invention is further explained in more detail below referring to examples and comparative examples, which are by way of illustration and not by way of limitation.

EXAMPLE 1

Into a Pyrex glass flask having an inner volume of 30 cm$^3$ were charged 6 cm$^3$ of N,N-dimethylformamide, 17.7 millimoles of cyclohexanone oxime, and 0.67 millimole of trimethyloxonium tetrafluoroborate, and the resulting mixture was subjected to reaction at 53° C. for 1 hour.

As a result, the conversion of cyclohexanone oxime was 17.8% and the selectivity of ε-caprolactam was 99.8%.

COMPARATIVE EXAMPLE 1

The same procedure as in Example 1 was repeated, except that a compound as shown in Table 1 was substituted for the N,N-dimethylformamide.

The results obtained are as shown in Table 1.

TABLE 1

| Run No. | Compound | Conversion of cyclohexanone oxime (%) |
|---|---|---|
| 1 | Dimethylsulfoxide | 0.2 |
| 2 | Formamide | 0.0 |
| 3 | N,N-Dimethylacetamide | 0.0 |
| 4 | Benzene | 0.0 |
| 5 | Hexane | 0.0 |

EXAMPLE 2

Into a Pyrex glass flask having an inner volume of 30 cm$^3$ were charged 3 cm$^3$ of N,N-dimethylformamide, 1.2 millimoles of ethyl p-toluenesulfonate, and 3.53 millimoles of cyclohexanone oxime, and the resulting mixture was subjected to reaction at 65° C. for 3 hours.

As a result, the conversion of cyclohexanone oxime was 9.6% and the selectivity of ε-caprolactam was 99.5%.

EXAMPLE 3

Into a Pyrex glass flask having an inner volume of 30 cm$^3$ were charged 2 cm$^3$ of N,N-dimethylformamide, 0.95 millimole of dimethylsulfuric acid, and 3.79 millimoles of cyclohexanone oxime, and the resulting mixture was subjected to reaction at 52° C. for 1 hour.

As a result, the conversion of cyclohexanone oxime was 14.1% and the selectivity of ε-caprolactam was 99.5%.

EXAMPLE 4

Into a Pyrex glass flask having an inner volume of 30 cm$^3$ were charged 3 cm$^3$ of N,N-dimethylformamide, 1.7 millimoles of 1,3-propanesultone, and 3.53 millimoles of cyclohexanone oxime, and the resulting mixture was subjected to reaction at 66° C. for 2 hours.

As a result, the conversion of cyclohexanone oxime was 26.1% and the selectivity of ε-caprolactam was 99%.

EXAMPLE 5

Into a Pyrex glass flask having an inner volume of 30 cm$^3$ were charged 3 cm$^3$ of N,N-dimethylformamide, 0.66 millimole of methyl trifluorosulfonate, and 3.53 millimoles of cyclohexanone oxime, and the resulting mixture was subjected to reaction at 65° C. for 1 hour.

As a result, the conversion of cyclohexanone oxime was 49.4% and the selectivity of c-caprolactam was 99%.

EXAMPLE 6

Into a Pyrex glass flask having an inner volume of 30 cm$^3$ were charged 2 cm$^3$ of N,N-dimethylformamide, 5.1 millimoles of epichlorohydrin, and 1.1 millimoles of boron trifluoride etherate, and the resulting mixture was treated at 50° C. for 1 hour to prepare a reaction accelerator. Thereto were then added 4 cm$^3$ of N,N-dimethylformamide and 17.7 millimoles of cyclohexanone oxime, and the resulting mixture was subjected to reaction at 55° C. for 1 hour.

As a result, the conversion of cyclohexanone oxime was 35.3% and the selectivity of ε-caprolactam was 99%.

EXAMPLE 7

The same procedure as in Example 6 was repeated, except that N-phenyl-N-methylformamide was substituted for the N,N-dimethylformamide and the reaction temperature was 52° C.

As a result, the conversion of cyclohexanone oxime was 12.7% and the selectivity of ε-caprolactam was 99%.

EXAMPLE 8

Into a Pyrex glass flask having an inner volume of 30 cm$^3$ were charged 2 cm$^3$ of N,N-diisopropylformamide, 2.0 millimoles of epichlorohydrin, and 0.54 millimole of boron trifluoride etherate, and the resulting mixture was treated at 50° C. for 1 hour to prepare a reaction accelerator. Thereto were then added 1 cm$^3$ of N,N-diisopropylformamide and 4.42 millimoles of cyclohexanone oxime, and the resulting mixture was subjected to reaction at 48° C. for 1 hour.

As a result, the conversion of cyclohexanone oxime was 41.9% and the selectivity of ε-caprolactam was 99%.

EXAMPLE 9

The same procedure as in Example 6 was repeated, except that an acid, ester, acid chloride or trifluoromethyl perchlorate as shown in Table 2 was substituted for the boron trifluoride etherate to effect reaction. Incidentally, when 97% sulfuric acid was used (Run No. 6), 97% sulfuric acid was added to dimethylformamide, thereafter benzene was added thereto, and the reaction mixture was then subjected to azeotropic dehydration, after which epichlorohydrin was added thereto to prepare a reaction accelerator.

The amounts of the reagents and starting oxime were as shown in Table 2.

The results obtained are shown in Table 2.

Incidentally, in each of Run Nos. 6 to 13 in Table 2, the selectivity of ε-caprolactam was 99% or more.

EXAMPLE 10

The same procedure as in Example 6 was repeated, except that an epoxide as shown in Table 3 was substituted for the epichlorohydrin.

The results obtained are shown in Table 3.

Incidentally, in each of Run Nos. 14 to 22 in Table 3, the selectivity of ε-caprolactam was 99% or more.

EXAMPLE 11

A 200-cm$^3$ round bottom flask was purged with nitrogen, and then charged with 30 cm$^3$ of dried N,N-dimethylformamide, 21.4 millimoles of propylene oxide, and 10.0 millimoles of boron trifluoride etherate, after which the resulting mixture was treated with at 50° C. for 1 hour, to prepare a reaction accelerator. Thereto were then added 61 cm$^3$ of N,N-dimethylformamide and 70.7 millimoles of cyclohexanone oxime, and the resulting mixture was subjected to reaction at 66° C. for 2 hours.

As a result, the conversion of cyclohexanone oxime was 76.1% and the selectivity of ε-caprolactam was 97.7%.

EXAMPLE 12

Into a Pyrex glass flask having an inner volume of 30 cm$^3$ were charged 2 cm$^3$ of N,N-dimethylformamide, 0.14 millimole of 12-tangstosilicic acid, and 2.6 millimoles of epichlorohydrin, and the resulting mixture was treated at 50° C. for 1 hour, after which 4 cm$^3$ of N,N-dimethylformamide and 17.7 millimoles of cyclohexanone oxime were added thereto. The resulting mixture was subjected to reaction at 50° C. for 1 hour.

As a result, the conversion of cyclohexanone oxime was 33.8% and the selectivity of ε-caprolactam was 99%.

EXAMPLE 13

Into a Pyrex glass flask having an inner volume of 30 cm$^3$ were charged 2 cm$^3$ of N,N-dimethylformamide, 0.1 millimole of 12-tungstophosphoric acid, and 2.6 millimoles of epichlorohydrin, and the resulting mixture was treated at 50° C. for 1 hour, after which 1 cm$^3$ of N,N-dimethylformamide and 8.84 millimoles of cyclohexanone oxime were added thereto. The resulting mixture was then subjected to reaction at 50° C. for 1 hour.

As a result, the conversion of cyclohexanone oxime was 17.6% and the selectivity of ε-caprolactam was 99%.

EXAMPLE 14

A 200-cm$^3$ round bottom flask was purged with and charged with 30 cm$^3$ of dried N,N-dimethylformamide. 24.0 millimoles of cyclohexene oxide, and 9.11 millimoles of boron trifluoride etherate, after which the resulting mixture was treated at 50° C. for 1 hour to prepare a reaction accelerator. Thereto was then added a solution of 70.7 millimoles of cyclohexanone oxime in 61 cm³ of dried N,N-dimethylformamide, after which the resulting mixture was subjected to reaction at 66° C. for 2 hours.

As a result, the conversion of cyclohexanone oxime was 82.1% and the selectivity of ε-caprolactam was 95.1%.

EXAMPLE 15

The same procedure as in Example 1 was repeated, except that reaction was conducted at 76° C. for 3 hours.

As a result, the conversion of cyclohexanone oxime was 92.1% and the selectivity of ε-caprolactam was 99.5%.

EXAMPLE 16

A 200-cm³ round bottom flask was purged with nitrogen, and charged with 30 cm³ of dried N,N-dimethylformamide, 21.4 millimoles of epichlorohydrin and 10 millimoles of fuming sulfuric acid ($SO_3$: 23% by weight), after which the resulting mixture was treated at 50° C. for 1 hour to prepare a reaction accelerator. Thereto was added a solution of 70.7 millimoles of cyclohexanone oxime in 61 cm³ of dried N,N-dimethylformamide, and the resulting mixture was subjected to reaction at 66° C. for 2 hours.

As a result, the conversion of cyclohexanone oxime was 99.2% and the selectivity of ε-caprolactam was 94.2%.

EXAMPLE 17

The same procedure as in Example 11 was repeated, except that phosphorus pentoxide was used as an acid component.

As a result, the conversion of cyclohexanone oxime was 90.4% and the selectivity of ε-caprolactam was 92.3%.

EXAMPLE 18

Into a Pyrex glass flask having an inner volume of 30 cm³ were charged 1 cm³ of N,N-dimethylformamide, 2.6 millimoles of epichlorohydrin, and 0.43 millimole of boron trifluoride etherate, and the resulting mixture was treated at 50° C. for 2 hours, after which 2 cm³ of N,N-dimethylformamide and 11.5 millimoles of 2-butanone oxime were added thereto. The resulting mixture was subjected to reaction at 52° C. for 2 hours.

As a result, the conversion of 2-butanone oxime was 10.5%, the total selectivity of N-methylpropionamide and N-ethylacetamide was 97.5%.

EXAMPLE 19

Into a Pyrex glass flask having an inner volume of 30 cm³ were charged 1 cm³ of N,N-dimethylformamide, 2.6 millimoles of epichlorohydrin and 0.51 millimole of boron trifluoride etherate, after which the resulting mixture was treated at 50° C. for 2 hours. Thereto were then added 2 cm³ of N,N-dimethylformamide and 16.9 millimoles of acetaldoxime, and the resulting mixture was subjected to reaction at 50° C. for 2 hours.

As a result, the conversion of acetaldoxime was 11.0% and the total selectivity of N-methylformamide and acetamide was 99.2%.

EXAMPLE 20

Into a Pyrex glass flask having an inner volume of 30 cm³ were charged 1 cm³ of N,N-dimethylformamide, 2.6 millimoles of epichlorohydrin, and 0.51 millimole of boron trifluoride etherate, and the resulting mixture was treated at 50° C. for 2 hours, after which 2 cm³ of N,N-dimethylformamide and 8.25 millimoles of syn-benzaldehyde oxime were added thereto. The resulting mixture was subjected to reaction at 50° C. for 2 hours.

As a result, the conversion of syn-benzaldehyde oxime was 17.5%, and the selectivity of N-phenylformamide was 99.5%.

EXAMPLE 21

To azeotropic distillation was subjected 2.0 g of proton type cation exchange resin (Amberlyst 15) to dehydrate the resin, and 6 cm³ of N,N-dimethylformamide and 1.0 cm³ of epichlorohydrin were added thereto. The resulting mixture was treated at 50° C. for 1 hour to prepare a solid reaction accelerator for oxime rearrangement.

A Pyrex glass reaction tube having an inner diameter of 8 mm was packed with the reaction accelerator thus obtained, and thereafter, a solution of 2.0 g of cyclohexanone oxime in 20 cm³ of N,N-dimethylformamide was fed to the tube from the top of the reaction tube at a rate of 1.76 cm³/hr to allow the solution to flow down while the reaction tube was maintained at 60° C.

After the solution had been allowed to flow down for 10 hours, the average conversion of cyclohexanone oxime was 91.5% and the selectivity of ε-caprolactam was 99.5%.

EXAMPLE 22

To 0.56 cm³ of glycidyl methacrylate were added 0.12 cm³ of divinylbenzene and 0.05 g of azobisisobutyronitrile, and the resulting mixture was subjected to polymerization at 70° C. for 2 hours to obtain a polymer.

The polymer thus obtained was pulverized, and then dispersed in 4.0 cm³ of N,N-dimethylformamide, after which 2.1 millimoles of boron trifluoride etherate was added thereto. The resulting mixture was treated at 55° C. for 2 hours to prepare a solid reaction accelerator for oxime rearrangement.

A Pyrex glass reaction tube having an inner diameter of 8 mm was packed with the solid reaction accelerator thus obtained, and a solution of 1.0 g of cyclohexanone oxime in 10 cm³ of N,N-dimethylformamide was fed to the reaction tube from the top of the tube at a rate of 1.76 cm³/hr to allow the solution to flow down while the reaction tube was kept at 60° C.

After the solution had been allowed to flow down for 5 hours, the average conversion of cyclohexanone oxime was 100% and the selectivity of s-caprolactam was 99.8%.

EXAMPLE 23

A 200-cm³ round bottom flask was purged with nitrogen, and charged with 30 cm³ of dried N,N-dimethylformamide, into which sulfur trioxide produced by blowing a nitrogen gas into fuming sulfuric acid heated at 120° C. was blown in an amount of 6.3 millimoles. In addition, 10.7 millimoles of epichlorohydrin was added thereto, and thereafter, the resulting mixture was stirred at 50° C. for 1 hour, to prepare a reaction accelerator. A solution of 70.7 millimoles of cyclohexanone oxime in 61 cm³ of N,N-dimethylformamide was then added thereto, and the resulting mixture was subjected to reaction at 66° C. for 1 hour.

As a result, the conversion of cyclohexanone oxime was 99.5%, the yield of ε-caprolactam was 94.4%, and the selectivity of s-caprolactam was 94.9%. The catalyst efficiency based on sulfur trioxide (turnover) was 10.6 (mole/mole).

EXAMPLE 24

A 200-cm$^3$ round bottom flask was purged with nitrogen, and charged with 30 cm$^3$ of dried N,N-dimethylformamide and 10 millimoles of dimethylsulfuric acid, after which the resulting mixture was stirred at 65° C. for 1 hour to prepare a reaction accelerator. Thereto was then added a solution of 70.7 millimoles of cyclohexanone oxime in 61 cm$^3$ of N,N-dimethylformamide and the resulting mixture was subjected to reaction at 65° C. for 2.5 hours.

As a result, the conversion of cyclohexanone oxime was 98.8%, the yield of $\epsilon$-caprolactam was 94.3% and the selectivity of $\epsilon$-caprolactam was 95.5%. The catalyst efficiency based on dimethylsulfuric acid (turnover) was 6.67 (mole/mole).

EXAMPLE 25

A 50-cm$^3$ round bottom flask was purged with nitrogen, and charged with 7.3 g (100 millimoles) of dried N,N-dimethylformamide, after which 12.6 g (100 millimoles) of dimethylsulfuric acid was dropwise added thereto at 60° C. with stirring over 30 minutes. The resulting mixture was stirred at 75° C. for 2 hours to prepare a reaction accelerator.

After a 200-cm$^3$ round bottom flask was purged with nitrogen, 30 cm$^3$ of dried N,N-dimethylformamide and 10 millimoles of the reaction accelerator prepared above were fed to the flask, and a solution of 70.7 millimoles of cyclohexanone oxime in 61 cm$^3$ of N,N-dimethylformamide was added thereto. The resulting mixture was subjected to reaction at 65° C. for 1 hour.

As a result, the conversion of cyclohexanone oxime was 99.6%, the yield of $\epsilon$-caprolactam was 92.0%, and the selectivity of $\epsilon$-caprolactam was 92.4%. The catalyst efficiency based on dimethylsulfuric acid (turnover) was 6.5 (mole/mole).

EXAMPLE 26

A 300-cm$^3$ round bottom flask was purged with nitrogen, and charged with 100 cm$^3$ of dried N,N-dimethylformamide and 5 millimoles of the reaction accelerator prepared in Example 25, after which a solution of 141.4 millimoles of cyclohexanone oxime in 80 cm$^3$ of N,N-dimethylformamide was added thereto. The resulting mixture was subjected to reaction at 85° C. for 1 hour.

As a result, the conversion of cyclohexanone oxime was 63.4%, the yield of $\epsilon$-caprolactam was 59.2%, and the selectivity of $\epsilon$-caprolactam was 93.5%. The catalyst efficiency based on dimethylsulfuric acid (turnover) was 16.8 (mole/mole).

EXAMPLE 27

A 200-cm$^3$ round bottom flask was purged with nitrogen, and then charged with 30 cm$^3$ of dried 1,2-dichloroethane and 10 millimoles of the reaction accelerator prepared in Example 25, after which a solution of 70.7 millimoles of cyclohexanone oxime in 61 cm$^3$ of 1,2-dichloroethane was added thereto. The resulting mixture was subjected to reaction at 65° C. for 1 hour.

As a result, the conversion of cyclohexanone oxime was 47.4%, the yield of $\epsilon$-caprolactam was 20.8%, and the selectivity of $\epsilon$-caprolactam was 43.8%. The catalyst efficiency based on dimethylsulfuric acid (turnover) was 1.5 (mole/mole).

EXAMPLE 28

A 200-cm$^3$ round bottom flask was purged with nitrogen, and then charged with 30 cm$^3$ of dried acetonitrile and 10 millimoles of the reaction accelerator prepared in Example 25, after which a solution of 70.7 millimoles of cyclohexanone oxime in 61 cm$^3$ of acetonitrile was added thereto. The resulting mixture was subjected to reaction at 65° C. for 1 hour.

As a result, the conversion of cyclohexanone oxime was 58.1%, the yield of $\epsilon$-caprolactam was 27.0%, and the selectivity of $\epsilon$-caprolactam was 46.5%. The catalyst efficiency based on dimethylsulfuric acid (turnover) was 1.9 (mole/mole).

EXAMPLE 29

A 100-cm$^3$ round bottom flask was purged with nitrogen and then charged with 15 cm$^3$ of dried N,N-dimethylacetamide and 5 millimoles of dimethylsulfuric acid, after which the resulting mixture was stirred at 75° C. for 1 hour to prepare a reaction accelerator. A solution of 70.7 millimoles of cyclohexanone oxime in 25 cm$^3$ of N,N-dimethylacetamide was added thereto. The resulting mixture was subjected to reaction at 65° C. for 1 hour.

As a result, the conversion of cyclohexanone oxime was 25.3%, the yield of $\epsilon$-caprolactam was 14.1%, and the selectivity of $\epsilon$-caprolactam was 55.8%. The catalyst efficiency based on dimethylsulfuric acid (turnover) was 2.0 (mole/mole).

EXAMPLE 30

A 200-cm$^3$ round bottom flask was purged with nitrogen, and then charged with 10 cm$^3$ of dried N,N-dimethylacetamide and 10 millimoles of dimethylsulfuric acid, after which the resulting mixture was stirred at 75° C. for 1 hour to prepare a reaction accelerator. A solution of 70.7 millimoles of cyclohexanone oxime in 85 cm$^3$ of N,N-dimethylformamide was added thereto. The resulting mixture was subjected to reaction at 65° C. for 1 hour.

As a result, the conversion of cyclohexanone oxime was 46.0%, the yield of $\epsilon$-caprolactam was 29.5%, and the selectivity of $\epsilon$-caprolactam was 64.2%. The catalyst efficiency based on dimethylsulfuric acid (turnover) was 1.9 (mole/mole).

TABLE 2

| Run No. | Feed conditions | | | | Conditions* | | Result |
| --- | --- | --- | --- | --- | --- | --- | --- |
| | Acid component | | ECH | Oxime/DMF. | Temp. | Time | Conversion |
| | Kind | mmol | (mmol) | (mmol/cm$^3$) | (°C.) | (hr) | of oxime (%) |
| 6 | 97% sulfuric acid | 1.5 | 5.1 | 7.57/1 | 51 | 2 | 64.8 |
| 7 | p-Toluenesulfonyl chloride | 0.7 | 1.3 | 2.65/1 | 53 | 2 | 81.7 |
| 8 | Sulfuric anhydride | 2.5 | 10.2 | 17.7/4 | 48 | 1 | 74.0 |
| 9 | Fluorosulfonic acid | 1.4 | 5.1 | 35.4/10 | 51 | 2 | 28.9 |

TABLE 2-continued

| Run No. | Acid component Kind | mmol | ECH (mmol) | Oxime/DMF. (mmol/cm³) | Temp. (°C.) | Time (hr) | Conversion of oxime (%) |
|---|---|---|---|---|---|---|---|
| 10 | Trifluoromethane sulfonic acid | 1.6 | 2.6 | 16.6/3 | 53 | 6 | 84.3 |
| 11 | Dimethylsulfuric acid | 0.83 | 5.1 | 7.57/3 | 51 | 4.5 | 25.6 |
| 12 | Sulfuryl chloride | 0.96 | 5.1 | 7.57/1 | 54 | 2 | 81.2 |
| 13 | Triphenylmethyl perchlorate | 0.17 | 2.6 | 17.7/4 | 48 | 1 | 2.7 |

Note:
ECH: Epichlorohydrin,
Oxime: Cyclohexanone oxime
DMF: Dimethylformamide (amount of DMF used in preparation of reaction accelerator: 2 cm³)
*Reaction conditions

TABLE 3

| Run No. | $BF_3$—$OEt_3$ (mmol) | Epoxide Kind | mmol | Oxime/DMF (mmol/cm³) | Temp. (°C.) | Time (hr) | Conversion of oxime (%) |
|---|---|---|---|---|---|---|---|
| 14 | 0.8 | 1,2-Epoxybutane | 4.6 | 35.4/10 | 55 | 2 | 22.1 |
| 15 | 0.76 | Styrene oxide | 2.6 | 16.8/4 | 50 | 1 | 13.0 |
| 16 | 1.19 | Glycidyl methacrylate | 2.2 | 17.7/4 | 54 | 1 | 56.6 |
| 17 | 1.16 | Glycidyl methyl ether | 3.3 | 17.7/4 | 53 | 1 | 36.9 |
| 18 | 0.50 | 1,2-Epoxyoctane | 2.0 | 8.84/1 | 49 | 2 | 16.2 |
| 19 | 0.38 | Cyclohexene oxide | 1.0 | 8.84/10 | 66 | 1 | 65.8 |
| 20 | 0.47 | 2,3-Epoxy-norbornane | 0.9 | 8.84/1 | 50 | 1 | 16.6 |
| 21 | 0.49 | 1,2-Epoxyhexadecane | 0.4 | 8.84/1 | 52 | 1 | 33.8 |
| 22 | 0.47 | N-(2,3-epoxy-propyl)-phthalimide | 1.0 | 8.84/1 | 50 | 1 | 43.0 |

Note:
Oxime: Cyclohexanone oxime,
DMF: Dimethylformamide (amount of DMF used in preparation of reaction accelerator: 2 cm³)
*Reaction conditions

What is claimed is:

1. A process for producing an amide which comprises rearranging a corresponding oxime selected from the group consisting of acetaldehyde oxime, acetone oxime, 2-butanone oxime, benzaldehyde oxime, acetophenone oxime, benzophenone oxime, cyclopentanone oxime, cyclohexanone oxime, and cyclododecanone oxime in the presence of a reaction accelerator consisting of an alkylating agent and an N,N-disubstituted formamide or N,N-disubstituted carboxylic acid amide represented by formula (1):

wherein $R^1$ and $R^2$, which may be the same or different, represent alkyl groups having 1 to 6 carbon atoms, or phenyl groups, and $R^3$ represents a hydrogen atom or an alkyl group having 1 to 6 carbon atoms.

2. The process according to claim 1, wherein the reaction temperature is 20° to 150° C.

3. The process according to claim 1, wherein the amount of the reaction accelerator is such that the oxime concentration in the reaction system is 1 to 30% by weight.

4. The process according to claim 1, wherein the amount of the reaction accelerator is such that the oxime concentration in the reaction system is 5 to 25% by weight.

5. The process according to claim 1, wherein the reaction accelerator is a solution of the alkylating agent in the N,N-disubstituted formamide or N,N-disubstituted carboxylic acid amide.

6. The process according to claim 1, wherein the reaction accelerator is in the form of a solution in a solvent.

7. The process according to claim 6, wherein the solvent is selected from the group consisting of hydrocarbon solvents, halogenated hydrocarbon solvents and non-protonic organic solvents.

8. The process according to claim 7, wherein the hydrocarbon solvents include benzene, toluene, hexane and heptane; the halogenated hydrocarbon solvents include 1,2-dichloroethane; and the non-protonic organic solvents include dimethylsulfoxide.

9. The process according to claim 1, wherein the N,N-di-substituted formamide is selected from the group consisting of N,N-dimethylformamide, N-N-diethylformamide, N,N-dipropylformamide, N,N-diisopropylformamide, N,N-dibutylformamide and N-phenyl-N-methylformamide, and the N,N-disubstituted carboxylic acid amide is selected from the group consisting of N,N-dimethylbutyramide, N,N-dimethylvaleramide, N,N-dimethylcapronamide, N,N-diethylacetamide, N,N-diisopropylacetamide and N,N-dimethylisobutyramide.

10. The process according to claim 1, wherein the alkylating agent is at least one compound selected from the group consisting of alkanesulfonic acid esters, aromatic sulfonic acid esters, trialkyloxonium salts and sulfuric acid esters.

11. The process according to claim 1, wherein the alkylating agent is a combination of a strong acid, an ester thereof or a strong acid chloride with an epoxy compound or a combination of triphenylmethyl perchlorate with an epoxy compound.

12. The process according to claim 1, wherein the alkylating agent is selected from the group consisting of methyl methanesulfonate, ethyl methanesulfonate, methyl trifluoromethanesulfonate, ethyl trifluoromethanesulfonate, methyl benzenesulfonate, ethyl benzenesulfonate, methyl toluenesulfonate, ethyl toluenesulfonate, trimethyloxonium tetrafluoroborate, trimethyloxonium hexafluoroantimonate, dimethyl sulfate, diethyl sulfate and 1,3-propanesulfone.

13. The process according to claim 11, wherein the strong acid is selected from the group consisting of boron trifluoride etherate, sulfuric acid, sulfuric anhydride, fuming sulfuric acid, perchloric acid, fluorosulfonic acid, a heteropolyacid, an alkanesulfonic acid, trifluoromethanesulfonic acid, an alkanesulfonic acid, trifluoromethanesulfonic acid, benzenesulfonic acid, toluenesulfonic acid, a sulfonic acid type ion exchange resin and phosphorus pentoxide.

14. The process according to claim 11, wherein the epoxy compound is selected from the group consisting of ethylene oxide, propylene oxide, 1,2-epoxybutane, isobutylene oxide, 1,2-epoxyoctane, 2,3-epoxyoctane, 1,2-epoxyhexadecane, cyclohexene oxide, 2,3-epoxynorbornane, styrene oxide, epichlorohydrin, epibromohydrin, 1,1,1-trichloro-2,3-epoxypropane, N-(2,3-epoxypropyl)phthalamide, glycidyl methacrylate, glycidyl methyl ether and a high molecular weight compound having an epoxy group.

15. The process according to claim 14, wherein the high molecular weight compound having an epoxy group is a polymer of glycidyl methacrylate.

* * * * *